(12) United States Patent
Mattke et al.

(10) Patent No.: US 8,871,969 B2
(45) Date of Patent: Oct. 28, 2014

(54) PROCESS FOR THE PRODUCTION OF POLYISOCYANATES

(75) Inventors: Torsten Mattke, Freinsheim (DE); Matthias Klötzer, Kroppen (DE); Robert Baumann, Mannheim (DE)

(73) Assignee: BASF SE, Ludwigshafen (DE)

( * ) Notice: Subject to any disclaimer, the term of this patent is extended or adjusted under 35 U.S.C. 154(b) by 329 days.

(21) Appl. No.: 13/483,747

(22) Filed: May 30, 2012

(65) Prior Publication Data

US 2013/0006013 A1  Jan. 3, 2013

Related U.S. Application Data

(60) Provisional application No. 61/491,232, filed on May 30, 2011.

(51) Int. Cl.
*C07C 263/06* (2006.01)

(52) U.S. Cl.
CPC ................................ *C07C 263/06* (2013.01)
USPC ............................ 560/344; 560/336; 560/338

(58) Field of Classification Search
USPC .......................................... 560/336, 338, 344
See application file for complete search history.

(56) References Cited

U.S. PATENT DOCUMENTS

| | | | |
|---|---|---|---|
| 2,145,242 A | 1/1939 | Arnold | |
| 4,203,916 A | 5/1980 | Zengel et al. | |
| 4,275,223 A | 6/1981 | Zengel et al. | |
| 4,418,211 A | 11/1983 | Zengel et al. | |
| 4,439,370 A | 3/1984 | Zengel et al. | |
| 4,457,871 A | 7/1984 | Zengel et al. | |
| 4,467,114 A | 8/1984 | Zengel et al. | |
| 4,486,603 A | 12/1984 | Zengel et al. | |
| 7,557,242 B2 | 7/2009 | Kohlstruk et al. | |
| 8,026,387 B2 * | 9/2011 | Kloetzer et al. | ............... 560/338 |
| 2005/0250960 A1 | 11/2005 | Kohlstruk et al. | |
| 2010/0274046 A1 | 10/2010 | Kloetzer et al. | |
| 2011/0207961 A1 | 8/2011 | Geissler et al. | |

FOREIGN PATENT DOCUMENTS

| | | |
|---|---|---|
| DE | 27 10 595 A1 | 9/1978 |
| EP | 0 018 588 A1 | 11/1980 |
| EP | 0 027 952 A1 | 5/1981 |
| EP | 0 028 338 A2 | 5/1981 |
| EP | 0 126 299 A1 | 11/1984 |
| EP | 0 566 925 A2 | 10/1993 |
| EP | 1 593 669 A1 | 11/2005 |
| JP | 62-246547 | 10/1987 |
| JP | 2005-320334 | 11/2005 |
| WO | WO 98/54129 | 12/1998 |
| WO | WO 2007/082818 A1 | 7/2007 |
| WO | WO 2011/015541 A1 | 2/2011 |

OTHER PUBLICATIONS

U.S. Appl. No. 13/661,652, filed Oct. 26, 2012, Leschinski, et al.
U.S. Appl. No. 13/587,378, filed Aug. 16, 2012, Mattke, et al.

* cited by examiner

*Primary Examiner* — Kamal Saeed
*Assistant Examiner* — Janet L Coppins
(74) *Attorney, Agent, or Firm* — Oblon, Spivak, McClelland, Maier & Neustadt, L.L.P.

(57) ABSTRACT

The invention provides a multistage process for continuously preparing organic polyisocyanates, preferably diisocyanates, more preferably aliphatic or cycloaliphatic diisocyanates, by reaction of the corresponding organic polyamines with carbonic acid derivatives and alcohols into monomeric polyurethanes of low molecular mass, and the dissociation of said polyurethanes. The invention further provides an associated preparation process in which at certain reaction stages the polyisocyanates prepared and unutilizable residues are removed and reusable by-products and intermediates are recycled to preliminary stages.

16 Claims, No Drawings

PROCESS FOR THE PRODUCTION OF POLYISOCYANATES

The invention provides a multistage process for continuously preparing organic polyisocyanates, preferably diisocyanates, more preferably aromatic, aliphatic or cycloaliphatic diisocyanates, by reaction of the corresponding organic polyamines with urea and secondary amines into monomeric polyureas of low molecular mass, and the dissociation of said polyureas. The invention further provides an associated preparation process in which at certain reaction stages the polyisocyanates prepared and unutilizable residues are removed and reusable by-products and intermediates are recycled to preliminary stages.

The industrial processes for preparing organic polyisocyanates, such as aromatic, aliphatic or cycloaliphatic polyisocyanates, for example, are based on the phosgenation of the corresponding organic polyamines to form polycarbamoyl chlorides and the dissociation of these chlorides to form the polyisocyanates and hydrogen chloride. Aside from the serious environmental, disposal and safety problems which the use of phosgene entails, these processes suffer from further critical disadvantages. For instance, aliphatic or cycloaliphatic polyisocyanates are prepared only with decidedly moderate space-time yields, owing to the relatively high basicity of the starting polyamines. A further disadvantage is the formation of unwanted by-products which, even when present in traces, can result in instances of severe discoloration of the polyisocyanates. The preparation of hexamethylene 1,6-diisocyanate (HDI), for example, produces a number of by-products, of which the most important, 6-chlorohexylisocyanate, possesses the disadvantage, moreover that considerable distillative outlay is needed to remove it from the HDI.

Such procedures suffer from the problems in particular of the high conversion of chlorine, via phosgene and carbamoyl chloride, into hydrogen chloride, the toxicity of the phosgene, and the corrosiveness of the reaction mixture, the instability of the solvents which are generally employed, and the formation of halogen-containing residues.

Although the dissociation of (cyclo)aliphatic and especially aromatic mono- and diurethanes into the corresponding isocyanates and alcohol is a long-established procedure and can be performed either in the gas phase at high temperatures or in the liquid phase at comparatively low temperatures, the unwanted secondary reactions, and particularly the tendency of the reaction mixtures to form coatings, resinous deposits, and blockages in reactors and work-up equipment are factors in particular which persistently detract from the economics of the operations.

Over recent decades, therefore, many attempts have been aimed at eliminating these disadvantages of the process by means of a simpler and improved process. For instance, for the preparation of aliphatic and/or cycloaliphatic di- and/or polyurethanes, in accordance with EP 18588 A1, or else as in EP 28338 A2, primary aliphatic and/or cycloaliphatic diamines and/or polyamines were reacted with O-alkylcarbamoyl esters in the presence of alcohols at temperatures from 160 to 300° C., both with and without catalyst. The resultant di- and/or polyurethanes can be converted into the corresponding isocyanates. The ammonia formed in the reaction of the amines can be removed.

Further publications deal with the partial replacement of urea and/or diamines by compounds containing carbonyl groups (e.g., EP 27952 or EP 126299). The phosgene-free process is comprehensively described in EP 566925 A2, for example.

A disadvantage of the latter process is the relatively long reaction time, which is given as being up to 50 hours.

Known from WO 2007/082818 (=US 2010/274046) is a process which does without the presence of alcohols and formation of urethanes as intermediate. There continues, however, to be a need for processes with improved yield.

A disadvantage of the above-described phosgene-free processes is that they can be used to prepare only isocyanates which are distillable without decomposition.

WO 98/54129 describes a process for decomposing diureas which are formed in each case from secondary amines. These secondary amines are very specific amines, in which the amino groups are substituted by a radical having a tertiary carbon atom, examples being tertiary butyl groups or 2,2-disubstituted piperidine groups.

The decomposition here takes place purely thermally, optionally in the presence of a carrier gas or of an inert solvent. A disadvantage here is that with this kind of reaction regime, the decomposition products—secondary amine and isocyanate—react with one another again quickly, not least on account of the high reactivity of the secondary amines.

The object of the present invention was to prepare organic polyisocyanates with high selectivity in improved yields, inexpensively and simply, without the use of costly and/or safety-jeopardizing starting materials or auxiliaries.

This object has been achieved by means of a process for preparing polyisocyanates by reaction of at least one polyamine with urea and at least one secondary amine to form the corresponding polyurea and subsequent acidic dissociation of the resulting polyureas into the corresponding polyisocyanates.

The invention further provides a multistage process for continuously preparing organic isocyanates by reaction of the corresponding organic polyamines with urea and at least one secondary amine to form the corresponding polyureas in at least one mixing apparatus with downstream reactor and the dissociation of said polyureas, said process comprising the following stages and comprising a) mixing together at least one organic polyamine with urea in the presence or preferably in the absence of at least one catalyst and with at least one secondary amine, optionally in the presence of at least one solvent, b) reacting the mixture obtained from a) in at least one following residence reactor or two or more residence reactors, c) removing the resultant ammonia at the same time as the reaction course in stage b) or subsequently, d) removing excess secondary amine, and other by-components which boil at temperatures lower than the polyureas, from the discharge from b), f) in a continuous dissociation apparatus, acidically dissociating the polyureas into the corresponding isocyanate and secondary amine, to give at least one isocyanate-containing stream and at least one secondary amine-containing stream, g) purifying the isocyanate-containing stream obtained from the dissociation f), by g1) removing solvent, if solvent was used beforehand,
   g2a) in the case of distillable isocyanates, subjecting them to distillative purification, or
   g2b) in the case of undistillable isocyanates, subjecting them to optional purification by nondistillative means,
and i) purifying the secondary amine-containing stream obtained from the dissociation f) and optionally recycling it.

The process of the invention features a better yield than processes known in the prior art, particularly the process known from EP 566 925.

Viewed in purely formal terms, the process of the invention can be outlined schematically by the following equation:

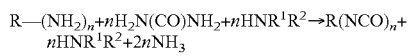

Suitability for preparing the monomeric polyureas $R(NH\!-\!CO\!-\!NR^1R^2)_n$ which can be used as intermediates in accordance with the invention is possessed by polyamines of the formula $R(NH_2)_n$, in which R is an n-valent, preferably trivalent or divalent, more preferably divalent organic radical, such as, for example, an optionally substituted—substituted, for example, by an alkyl group—aromatic, or a linear or branched-chain aliphatic or optionally substituted cycloaliphatic radical.

Examples of suitable aromatic polyamines include 2,4- and 2,6-tolylenediamine, 4,4'-, 2,4'- and 2,2'-diaminodiphenylmethanes, and the corresponding isomer mixtures.

It is an embodiment of the present invention that the process of the invention can be used for the conversion into the corresponding isocyanates even of aromatic amines which are polyamine mixtures of the diphenylmethane series, of the kind obtainable conventionally by polycondensation of formaldehyde with aniline.

Examples of aliphatic or cycloaliphatic polyamines contemplated include the following: butane-1,4-diamine, pentane-1,5-diamine, 2-ethylbutane-1,4-diamine, octane-1,8-diamine, decane-1,10-diamine, dodecane-1,12-diamine, cyclohexane-1,4-diamine, 2-methyl-, 4-methyl-cyclohexane-1,3-diamine, 1,3- and 1,4-diaminomethylcyclohexane, and also 4,4'- or 2,4'-di-(isocyanatocyclohexyl)methane. Finding use preferably are 2-methylpentane-1,5-diamine, 2,2,4- and/or 2,4,4-trimethylhexane-1,6-diamine, and more particularly 4,4'- or 2,4'-di(iso-cyanatocyclohexyl)methane, hexane-1,6-diamine, and 3-aminomethyl-3,5,5-trimethylcyclohexylamine.

Suitable secondary amines include in principle those secondary amines which are stable under the reaction conditions, i.e., which under the reaction conditions undergo hourly decomposition to an extent of less than 5 mol %, preferably less than 3, more preferably less than 2, and very preferably less than 1 mol %, based on the material employed, more particularly those secondary amines having a molar weight below 500 g/mol that have no further functional groups and apart from the secondary amino function carry exclusively hydrocarbon radicals and ether groups, preferably exclusively hydrocarbon radicals.

It is preferred to select those secondary amines whose boiling points are sufficiently far removed from the boiling point of the polyisocyanate, preferably diisocyanate, obtained by the dissociation, thereby allowing highly quantitative separation of the polyisocyanate, preferably diisocyanate dissociation product, from the secondary amine dissociation product by distillation. The difference in boiling point between secondary amine and isocyanate is preferably at least 20° C., more preferably at least 30° C., and very preferably at least 40° C.

The secondary amines are preferably amines of formula $HNR^1R^2$, in which $R^1$ and $R^2$ independently of one another may denote alkyl having 1 to 20, preferably 1 to 10, and more preferably 1 to 6 carbon atoms, cycloalkyl having 3 to 12, preferably 5 to 12, more preferably 5 to 6 carbon atoms, aryl having 6 to 14, preferably 6 to 10, more preferably 6 to 8 carbon atoms, or an aralkyl radical which has 6 to 14, preferably 6 to 8, carbon atoms in the aryl and 1 to 6, preferably 1 to 3, carbon atoms in the alkyl radical, or the radicals $R^1$ and $R^2$ together may form a ring which with the inclusion of the nitrogen atom is five- to twelve-membered, preferably five- to six-membered, it being possible for the radicals, less preferably, additionally to have ether groups.

Examples of alkyl groups are methyl, ethyl, isopropyl, n-propyl, n-butyl, isobutyl, sec-butyl, tert-butyl, n-hexyl, n-heptyl, 2-ethylhexyl, 2-propylheptyl, n-octyl, n-decyl, n-dodecyl, n-tetradecyl, n-hexadecyl, n-octadecyl, n-eicosyl, preferably methyl, ethyl, isopropyl, n-propyl, n-butyl, tert-butyl and n-hexyl, more preferably methyl, ethyl, isopropyl and n-butyl.

Examples of cycloalkyl groups are cyclopentyl, cyclohexyl, cyclooctyl and cyclododecyl, preferably cyclopentyl and cyclohexyl.

Examples of aryl groups are phenyl, tolyl, xylyl and naphthyl, preferably phenyl and tolyl, and more preferably phenyl.

Examples of aralkyl groups are benzyl, phenethyl, and 2- or 3-phenylpropyl, preferably benzyl and phenethyl, more preferably benzyl.

Preferred secondary amines are dimethylamine, diethylamine, di-n-propylamine, di-isopropyl-amine, di-n-butylamine, dihexylamine, dioctylamine, ethylmethylamine, isopropylmethylamine, n-butylmethylamine, tert-butylmethylamine, isopropylethylamine, n-butylethylamine, tert-butyl-ethylamine, morpholine, piperidine and pyrrolidine; preferred are dimethylamine, diethylamine, di-n-propylamine, diisopropylamine, di-n-butylamine, piperidine and pyrrolidine, more preferably dimethylamine, diethylamine, diisopropylamine, and di-n-butylamine, very preferably dimethylamine and di-n-butylamine, and more particularly di-n-butylamine.

It cannot be ruled out that sterically bulky primary amines may react in the sense of the invention, like the secondary amines recited above, examples being tert-butylamine or isopropyiamine, but preference in the context of the present invention is given to secondary amines.

The individual stages of the process are described below:
a) Mixing of the Reaction Components For the preparation of the polyureas in reaction stage (a), the polyamines are mixed together with urea and at least one, preferably just one, secondary amine in a molar ratio of polyamine, urea, and secondary amine of 1:2 to 20:5 to 40, preferably 1:2.0 to 5:6 to 10, at temperatures of 50-300° C. and more particularly at 130-220° C., under a pressure of 0.1 to 30 bar, preferably 1-10 bar.

In one preferred embodiment, in stage a), all three starting components, polyamine, urea and secondary amine, are mixed together.

It is, however, also possible first to mix together two of these three starting components, and then to mix the resulting mixture with the third starting component. Among the three such possible permutations, it is preferred first to mix polyamine and secondary amine and then to mix the resulting mixture with urea.

Urea here may be metered alternatively as a melt, as a solid or as a solution in a solvent, preferably as a melt or as a solution.

The mixing in stage (a) may be carried out in the presence of substituted ureas, usefully in an amount of 0.1 to 30 mol %, preferably 1 to 10 mol %, based on the polyamine, preferably diamine. Use is made more particularly here of mixtures of substituted ureas in the stated proportions. As substituted ureas it is preferred to employ those whose substitution patterns match that of the secondary amine employed, i.e., the formal reaction products of urea with one or two equivalents of secondary amine.

The mixing in stage (a) may take place optionally in the presence of at least one solvent.

Suitable solvents are preferably hydrocarbons, optionally substituted by halogen atoms, such as, for example, hexane, benzene, nitrobenzene, anisole, chlorobenzene, chlorotoluene, o-dichlorobenzene, trichlorobenzene, diethyl isophthalate (DEIP), tetrahydrofuran (THF), dimethylformamide (DMF), xylene, chloronaphthalene, decahydronaphthalene, and toluene. A particularly preferred solvent used is dichlorobenzene.

As already maintained, the mixing in stage (a) or else the reaction in stage b) can also take place in the presence of catalysts. These catalysts are employed usefully in amounts of 0.001% to 20% by weight, preferably 0.001% to 1% by weight, more particularly 0.002% to 0.1% by weight, based on the weight of the polyamine.

Suitable catalysts are organic or inorganic compounds which comprise one or more cations, preferably one cation, of metals from groups IA, IB, IIA, IIB, IIIB, IVA, IVB, VA, VB, VIB, VIIB, and VIIIB of the Periodic Table of the Elements, defined as per Handbook of Chemistry and Physics 14th Edition, published by Chemical Rubber Publishing Co., 23 Superior Ave. N.E., Cleveland, Ohio. Examples include the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron and cobalt.

The catalyst may further comprise at least one anion, halides for example, such as chlorides and bromides, sulfates, phosphates, nitrates, borates, alkoxides, phenoxides, sulfonates, oxides, hydrated oxides, hydroxides, carboxylates, chelates, carbonates, and thio- or dithiocarbamates.

The catalysts can also be employed, without perceptible significant disadvantages, in the form of their hydrates or ammoniates.

Typical catalysts include by way of example the following compounds: lithium methoxide, lithium ethoxide, lithium propoxide, lithium butoxide, sodium methoxide, potassium tert-butoxide, magnesium methoxide, calcium methoxide, tin (II) chloride, tin(IV) chloride, lead acetate, lead phosphate, antimony(III) chloride, antimony(V) chloride, aluminum acetylacetonate, aluminum isobutoxide, aluminum trichloride, bismuth(III) chloride, copper(II) acetate, copper(II) sulfate, copper(II) nitrate, bis(triphenylphosphinoxido)copper (II) chloride, copper molybdenate, silver acetate, gold acetate, zinc oxide, zinc chloride, zinc acetate, zinc acetonylacetate, zinc octoate, zinc oxalate, zinc hexylate, zinc benzoate, zinc undecylenate, cerium(IV) oxide, uranyl acetate, titanium tetrabutoxide, titanium tetrachloride, titanium tetraphenoxide, titanium naphthenate, vanadium(III) chloride, vanadium acetylacetonate, chromium(III) chloride, molybdenum(VI) oxide, molybdenum acetylacetonate, tungsten (VI) oxide, manganese(II) chloride, manganese(II) acetate, manganese(III) acetate, iron(II) acetate, iron(III) acetate, iron phosphate, iron oxalate, iron(III) chloride, iron(III) bromide, cobalt acetate, cobalt chloride, cobalt sulfate, cobalt naphthenate, nickel chloride, nickel acetate, and nickel naphthenate and also mixtures thereof.

Preferred catalysts include, by way of example, the following compounds: lithium butoxide, aluminum acetylacetonate, zinc acetylacetonate, titanium tetrabutoxide, and zirconium tetrabutylate.

The reactant streams may optionally be mixed in a suitable special mixing apparatus which is distinguished by short mixing times in order then to achieve the substantial conversion subsequently, in stage b), in at least one reactor.

The mixing time in this mixing apparatus is typically from 0.0001 s to 60 s, preferably from 0.0005 to 30 s, more preferably from 0.001 to 20 s, very preferably from 0.005 to 10 s, and more particularly from 0.007 to 5 s. The mixing time is the time elapsing from the start of the mixing operation until 97.5% of the fluid elements of the mixture obtained have a mixture fraction which, relative to the value of the theoretical end value of the mixture fraction of the mixture obtained, when the state of perfect mixing has been attained, deviates by less than 2.5% from this end value of the mixture fraction (with regard to the concept of the mixture fraction, see, for example, J. Warnatz, U. Maas, R. W. Dibble: Verbrennung [Combustion], Springer Verlag, Berlin Heidelberg New York, 1997, $2^{nd}$ edition, p. 134.).

As mixing apparatus it is preferred to use a mixing circuit, a stirring container, a mixing pump or a jet mixing apparatus, examples being coaxial mixing jets, Y or T mixers, or a vortex impinging jet mixing configuration, preferably a mixing circuit, a stirring container, a mixing pump or a nozzle mixing apparatus.

The temperature of the discharge material from the mixing apparatus is generally from 25 to 240° C., preferably 30-190 and more preferably 40-180° C.

The discharge material from the mixing apparatus, before being introduced into stage b), may be brought to the temperature desired there, by means of a heat exchanger.

During the mixing there may already be a reaction of polyamine and urea and also, possibly, with secondary amine; generally speaking, this is not a problem.

b) Reaction of the Mixture from a)

The mixture leaving the mixing apparatus is then supplied to at least one, preferably just one, or two or more residence reactors, which are operated with two phases (gaseous/liquid), and in which the gas phase is passed cocurrently with the liquid phase.

Where the residence reactor in stage b) is sufficiently backmixed, taking the form, for example, of a stirred tank, it may be of advantage to combine stages a) and b), i.e., to carry out the mixing within stage b), in a stirred tank, for example.

In the residence reactor as observed above, at one or more points, as for example at the beginning and in the middle of the reactor, it is optionally possible to meter in further urea and/or secondary amine or, preferably, polyamine.

The average residence time in the reactor is generally 10 minutes to 8 hours, preferably 20 minutes to 5 hours, more preferably 30 minutes to 3 hours.

In order to keep the gas load low for the following stage, the discharge material from the reactor may be supplied, in one preferred embodiment to a phase separator, and the liquid phase taken from the phase separator may then be supplied to the following stage.

A phase separator of this kind is a vessel in which phase separation between gas phase and liquid phase is achieved through the calming of the two-phase flow emerging from the cocurrent reactor.

The phase separator may be of isothermal or, preferably, heated design, in order to prevent the precipitation of by-products that are of low solubility. Heating may take place, for example, via the jacket or via a circuit with an external heat exchanger. If an external heat exchanger is used, standard insulation of the heat exchanger is sufficient.

The temperature in the reactor or reactor combination and in any phase separator present is generally between 50° C. and 300° C., preferably between 180° C. and 220° C.

The pressure in stage b) is generally between 0.1 bar abs and 30 bar abs, and preferably between 3 and 20 bar abs.

The residence time in stage b) is selected such that the conversion, based on amino groups in the polyamine used relative to polyurea, after departure from the reactor is at least 95%, preferably at least 98%, more preferably at least 99%, and very preferably at least 99.5%.

The overall residence time in stages a) and b) together is typically less than 8 hours, preferably less than 7 hours, and more preferably less than 6 hours.

For the complete conversion of the polyamines to the polyurea, in one preferred variant, the ammonia formed during the reaction is supplied directly, after each reactor section, to an ammonia removal facility or, when mixing reactors in series are being used, is removed in each reaction unit in parallel with the progress of the reaction.

If, after departure from the reactor or reactor combination, the conversion, based on amino groups in the polyamine used relative to urea groups, is still not complete, and is less than 95%, for example, then the discharge material may be reacted further.

For this purpose, in order to complete the conversion, the reaction mixture may be allowed to continue reaction in a further reactor, preferably until the conversion is 98% or more.

In one possible embodiment of the present invention it is also possible to carry out stages a) and b) in a stirred tank or in a cascade of stirred tanks, preferably in one to four stirred tanks, more preferably one to three stirred tanks, more preferably two to three stirred tanks, and very preferably two stirred tanks. In this case, the first stirred tank functions at least in part as stage a), and the remaining stirred tanks function as stage b).

The reaction conditions in such an embodiment otherwise correspond to those described above.

c) Ammonia Removal

For the removal of the ammonia it is useful to use columns, the ammonia being removed preferably by distillation. In this way, effective separation is achieved between the secondary amine and ammonia. Removal takes place typically in a pressure range of 0.01-20 bar, preferably at 0.04-15 bar. The necessary temperatures are guided by the secondary amine or mixture thereof that is used. For di-n-butylamine, the temperature, for example, is 210° C., preferably 190° C.

It has been found advantageous to remove the ammonia formed from the reaction mixture immediately, thereby making it possible to prevent deposition of ammonium carbamate, which is formed in minimal amounts from ammonia and carbon dioxide as a result of decomposition of urea by traces of water.

The ammonia removed may have a secondary amine content of up to 70%, preferably up to 65%, more preferably up to 55%, very preferably up to 50%, by weight. In this case it may be useful to work up to this mixture of secondary amine and ammonia, to recover the secondary amine.

This distillation unit for the removal of ammonia, optionally containing secondary amine, from the reaction mixture is a unit of conventional construction and has the typical internals. Column internals contemplated include in principle all commonplace internals, examples being trays, ordered packing and/or random packing. Among trays, preference is given to bubble cap trays, sieve trays, valve trays, Thormann trays and/or dual-flow trays; among the random packing, preference is given to packing with rings, helices, saddle bodies, Raschig, Intos or Pall rings, barrel saddles or Intalox saddles, Top-Pak, etc., or braids. It is preferred to use trays, more preferably bubble cap trays.

d) Removal of the Excess Secondary Amine

From the ammonia-depleted reaction mixture which is obtained, the secondary amine that remains, and optionally the solvent, if used, are removed and preferably recycled to reaction stages (a) and/or (b).

If solvent is used in the dissociation (stage f), see below), then complete removal of this solvent at this stage d) is less preferred.

For the removal of the amine, the reaction mixture is advantageously depressurized from the pressure level of reaction stage (b) to a pressure in the range from 1 to 2000 mbar, preferably from 10 to 900 mbar. This produces gaseous vapors ($d_L$), which contain the predominant amount of secondary amine and also 10% to 99%, preferably 50% to 95%, by weight of solvent, and a liquid discharge material, which is composed substantially of the monomeric polyurea, preferably diurea, and may comprise high-boiling oligomers.

The vapors ($d_L$) obtained may be separated optionally in downstream purification stages, usefully distillative purification stages, preferably by rectification, and the products of value that are isolated in this operation, secondary amine and removed solvent, may be recycled, individually or as a mixture, preferably to reaction stage (a) for the formation of the monomeric polyureas.

In one preferred embodiment of the present invention, secondary amine and solvent, if used, are not separated, but are instead recycled as a mixture. For the distillative removal of the secondary amine or mixture thereof it is common to use a flash evaporator. This apparatus may be a vessel or a combination of vessel and column, preferably a column, from the top of which the secondary amine or mixture thereof can be taken off, and from the bottom of which the polyurea can be taken off. The column top product may comprise not only the secondary amine but also further compounds which boil at points lower than that of the polyurea, and which may be returned, for example, to stage b). The separation takes place in a pressure range from 0.001 to 1 bar, preferably at 0.02-0.8 bar.

The distillation bottom product may generally also comprise solvent, which can be passed without disadvantages to the downstream dissociation f), particularly when the dissociation f) is carried out acidically with phase separation.

f) Polyurea Dissociation

The reaction mixture comprising polyureas obtained in reaction stage (b) is subjected to dissociation in a suitable apparatus, preferably in a solvent or solvent mixture in liquid phase, in the presence of acids, at temperatures from 20 to 250° C., preferably 100 to 200° C., and under a pressure of 0.1-5 bar, preferably in the range of 0.3-2 bar, this dissociation being continuous and being acidic.

Acids used may be organic or inorganic Brønsted acids, preferably those having a $pK_a$ of not more than 5, more preferably with a $pK_a$ of not more than 4, and very preferably with a $pK_a$ of not more than 3. Inorganic Brønsted acids are preferred.

In one preferred embodiment the acids are used in anhydrous form.

Preferred examples of such acids are sulfuric acid, phosphoric acid, nitric acid, hydrochloric acid, and hydrobromic acid. Sulfuric acid and hydrochloric acid are particularly preferred, hydrochloric acid very preferred. More particularly, use is made of gaseous hydrogen chloride.

In order to shift the reaction equilibrium from the polyurea to the isocyanate, the molar ratio of acid to urea (per urea group) ought to be at least 2:1, preferably at least 3:1. The conversions in the reaction installation are dependent, generally heavily so, on the acid excess employed, and may be selected largely freely. They are situated usefully in a range from 10% to 100%, preferably 80% to 99%, by weight of the amount of polyurea supplied.

As acids for the chemical dissociation of the polyureas it is possible for the aforementioned organic and inorganic compounds that catalyze urea formation to be used.

Suitable solvents are preferably hydrocarbons, optionally substituted by halogen atoms, such as, for example, hexane, benzene, nitrobenzene, anisole, chlorobenzene, chlorotoluene, o-dichlorobenzene, trichlorobenzene, diethyl isophthalate (DEIP), tetrahydrofuran (THF), dimethylformamide (DMF), xylene, chloronaphthalene, decahydronaphthalene, and toluene. A particularly preferred solvent used is dichlorobenzene. One embodiment uses the same solvent as in stages a) and b).

The dissociation can be carried out in a stirred tank or cascade of stirred tanks or in a tube reactor having a Bodenstein number of up to 5, preferably in an individual stirred tank. The average residence time is up to one hour, preferably up to 40 minutes, more preferably up to 15, and very preferably up to 10 min. An alternative possibility is to use the reactor constructions that are known to the skilled person for gas-liquid reactions, such as bubble columns or reaction columns.

In a further preferred embodiment it is possible with preference when using at least one, preferably precisely one, gaseous acid, more particularly hydrogen chloride as acid, to carry out the dissociation in a mixing pump or in a nozzle mixing apparatus, examples being coaxial mixing nozzles, Y- or T-mixers, or a vortex impinging jet mixing configuration, such devices effecting a rapid phase transition from the gas phase to the liquid phase.

The temperature in the dissociation in this case is generally from 100 to 200° C., preferably 120-190° C., and more preferably 140-180° C. In this embodiment, the reaction time may be significantly less than 10 minutes, preferably up to 5 minutes, more preferably up to 3 minutes, and very preferably up to 1 minute.

The discharge material from the dissociation reactor is then passed to at least one, preferably just one, separation stage, in which an organic, liquid, polyisocyanates-comprising phase is separated from a second phase which comprises the secondary amine in the form of its ammonium salt with the acid residue.

The separation may be a solid-liquid separation, such as centrifugation or filtration, for example, preferably a filtration of the solid salt phase. In order to reduce the solubility, the reaction mixture is optionally cooled again prior to the solid-liquid separation.

It is, however, also possible for any desired kind of a crystallization and phase separation to be employed, in suitable apparatus known to the skilled person, such as crystallizers, for example. The reaction discharge material may alternatively be separated extractively by addition of a suitable extractrant.

g) Isocyanate Purification

The polyisocyanate obtained from stage f), preferably in the form of a solution in a solvent from the acidic dissociation from stage f), is purified in stage g).

If a solvent has been used in one of the preceding reaction steps, then it may be removed by distillation in a first purification step g1). The solvent thus removed may then be passed preferably into stage a) and/or b) and/or f), if needed there.

Subsequently, in the case of distillable isocyanates, they can then be purified by distillation in a step g2a), as follows:

In a subsequent distillation, the crude isocyanate mixture is freed from recombination products, by-products, and, if present, traces of solvent. The by-products are preferably recycled to reaction steps a) and/or b). A portion may also be removed.

The distillation takes place advantageously by means of one or more distillation columns, preferably by rectification at temperatures from 100 to 220° C., preferably 120 to 170° C., under a pressure of 1 to 200 mbar, preferably 5 to 50 mbar, to give low boilers ($g_L$) and a crude polyisocyanate mixture ($g_M$) having a polyisocyanate content of 85% to 99%, preferably of 95% to 99%, by weight. The relatively high-boiling by-products ($g_H$) that are obtained in the distillative separation, and more particularly the undissociated and partially dissociated polyureas, are passed to the dissociation (f) or, preferably, removed.

The index "L" is used here to label low-boiling streams in the individual stages, with the indices "H" used for high-boiling and "M" for middle-boiling streams.

The crude polyisocyanate mixture ($g_m$) obtained preferably by rectification may be purified further in a further distillation at a temperature of 100 to 180° C. and under a pressure of 1 to 50 mbar, the resulting pure polyisocyanate stream possessing a purity of at least 98%, more particularly more than 99%, by weight.

According to other process variants, however, the bottom fraction ($g_H$) may also be recycled to the distillation column (d) for the separation of crude polyisocyanate and secondary amine, or to reaction stages (a) and/or (b), the formation of polyurea. Also possible is a division of the bottom fraction into 2 or 3 product streams, which are recycled preferably to the polyurea formation stage (a) and to the dissociation apparatus (f), and also, optionally, to the distillation column (g).

Where the isocyanate prepared is a nondistillable isocyanate, it may optionally be purified in a stage g2b) by a nondistillative method, as for example by extraction or scrubbing with a solvent.

i) Recovery of the Secondary Amine

The product obtained from stage f), in the form of a salt of secondary amine and the acid used for the dissociation, in a solvent, may in one preferred embodiment be worked up by being liberated with a base, as for example with hydroxides, oxides, carbonates or hydrogen carbonates of alkali metals or alkaline earth metals, preferably sodium hydroxide, sodium hydrogen carbonate, sodium carbonate or milk of lime.

Preference, however, is given to liberation using ammonia, more preferably at least partly using the ammonia removed in stage c).

In order to allow the stronger base, secondary amine, to be displaced with the weaker base, ammonia, it is necessary to use an excess of ammonia over the secondary amine, of, for example, from 1:1 to 20:1, and preferably from 1.5:1 to 15:1.

The liberation takes place at a temperature of 0 to 60° C., preferably 0 to 40° C., in a residence time of 10 min to 3 hours, preferably 20 to 120 min, and more preferably 30 to 90 min.

This produces a solution of the liberated secondary amine in the solvent, which is removed from the ammonium salt of the acid by solid-liquid phase separation, preferably by centrifugation or filtration.

The liberated secondary amine is subsequently returned preferably to the reaction.

An alternative option is to subject the salt, formed from the secondary amine and the acid used for the dissociation, to—optional—thermal separation, in a solvent.

For this purpose, the salt, optionally in a solution, is heated to above its decomposition temperature, and the decomposition products are separated thermally. This can be done, for example, in a rectifying column. However, different combinations of thermal dissociation and subsequent separation by adsorption, absorption, and partial condensation are also possible. With the multistage process of the invention for continuously preparing organic polyisocyanates, with recycling and removal of the by-products, it is possible to prepare polyisocyanates, preferably diisocyanate, with high selectivity and in very good yields.

The process of the invention is especially suitable for preparing aliphatic diisocyanates, such as 2-methylpentane 1,5-diisocyanate, isomeric aliphatic diisocyanates having 6 carbon atoms in the alkylene radical, and mixtures thereof, and preferably hexamethylene 1,6-diisocyanate, and cycloaliphatic diisocyanates, more particularly 3-isocyanatomethyl-3,5,5-trimethylcyclohexyl isocyanate, by an economic method. Also conceivable, however, is the preparation of 2,4- and 2,6-tolylene diisocyanate, and also of polymeric diphenylmethane diisocyanate (pMDI).

The polyisocyanates prepared are outstandingly suitable for the production of plastics comprising urethane, isocyanurate, amide and/or urea groups, by the polyisocyanate polyaddition process. They find use, furthermore, in the preparation of polyisocyanate mixtures modified with urethane, biuret and/or isocyanurate groups. Polyisocyanate mixtures of this kind, comprising aliphatic or cycloaliphatic diisocyanates, are used more particularly for the production of light-resistant polyurethane paints and coatings.

The examples below are intended to illustrate the invention, but not to confine it to these examples.

EXAMPLES

A) Preparation of the Urea Mixture

In a pressure reactor, 26.7 g of urea, 17.2 g of 1,6-hexamethylenediamine, and 154.1 g of dibutylamine were mixed with 316.6 g of dichlorobenzene solvent and thereafter heated rapidly to 215° C. The initial pressure established, of 7.8 bar, was lowered to 1.5 bar over a reaction time of two hours. The vapors departing the reactor were cooled in a water-cooled condenser, and the accumulating liquid was returned to the reactor. The ammonia removed in this way was passed to a waste gas treatment system. The concentration of the urea (1,1-dibutyl-3-[6-(3,3-dibutylureido)hexyl]urea), analyzed by means of GPC, was approximately 12.6% by weight. This corresponded to a yield of 99.7 mol %.

B) Removal of the Secondary Amine

The mixture from A) was freed from a major part of the dibutylamine under reduced pressure at approximately 25 mbar. GC analysis found about 50% by weight of amine in the distillate. The remainder was solvent.

C) Dissociation to the Isocyanate

The mixture from B) that remained in the bottoms was introduced into a glass laboratory flask with stirrer and gas inlet tube. At a temperature of around 150° C., gas was passed into the flask from a hydrogen chloride bottle, with mixing in the flask being thorough. The metering rate was approximately 20 liters/h. After around two hours, hexamethylene diisocyanate was analyzed in the mixture by means of GC. The yield, based on the urea, reached values of 97 mol %.

D) Recovery of the Secondary Amine

The recovery of the dibutylamine from the reaction mixture from C) was accomplished initially by filtration removal of the salt formed in C). The solid was slurried in dichlorobenzene, with addition of about 90% by weight of solvent. The resulting slurry was reacted with ammonia gas (20 liters/h) in a flask at 20° C., with thorough mixing by means of a stirrer, to form the amine and ammonium chloride. The yield of dibutylamine formed, based on salt, was 97%.

In two laboratory experiments, examples 1 and 3 of WO 98/54129 were reproduced: Preparation of the Ureas to be Dissociated: 3.56 g (0.041 mol) of N-methyl-tert-butylamine were introduced in 50 g of dichlorobenzene in a 250 ml four-neck flask and heated to 90° C. in the absence of oxygen. Metered in to this initial charge at 90° C. over 30 minutes were 5.11 g (0.02 mol) of 4,4'-methylenebisphenyl isocyanate (MDI) in 50 ml of dichlorobenzene, in a heated dropping funnel, after which the mixture was allowed to react at 90° C. for 2 hours. The clear solution was cooled, during which a colorless precipitate was formed, which was isolated by filtration and washed with n-hexane.

Drying gave 8.35 g of the corresponding MDI urea.

Reproduction of Example 1 of WO 98/54129

1.05 g of 4,4'-MDI urea were weighed out into a flask with a top-mounted distillation bridge, and the melt was subjected to thermal treatment as indicated in Example 1 of WO 98/54129, at 215 to 221° C. and 0.3 to 0.4 mbar. An overhead temperature of 45 to 55° C. was observed. Despite long heating (for about an hour), the amount of distillate that could be distilled off was only 0.027 g, with an N-methyl-tert-butylamine content of 91.1%. This corresponds to a yield of around 6 mol %. A subsequent removal of MDI, as described, was unsuccessful.

Reproduction of Example 3 of WO 98/54129

In accordance with example 3 of WO 98/54129, 5.64 g of MDI urea were heated at boiling under atmospheric pressure with 50.76 g of dichlorobenzene (DCB). With the objective of a constant volume in the distillation still with top-mounted distillation bridge, continuous metered addition of fresh solvent took place at about 185° C. In this way, 100 ml of DCB were metered in over the course of about 1.5 hours. After this time, an NCO value of 1.41% was analyzed in the liquid phase and 1.23% of N-methyl-tert-butylamine were analyzed in the distillate. The NCO value corresponds to about 0.0167 mol of 4,4'-MDI. The yield therefore corresponds to about 79 mol %. The stated yield of 98% was not achieved.

The invention claimed is:

1. A process for preparing polyisocyanates by reaction of at least one polyamine with urea and at least one secondary amine to form the corresponding polyurea and subsequent dissociation of the resulting polyureas into the corresponding polyisocyanates, which comprises a multistage process for continuously preparing organic isocyanates by reaction of the corresponding organic polyamines with urea and at least one secondary amine to form the corresponding polyureas in at least one mixing apparatus with downstream reactor and the dissociation of said polyureas, said process
 a) mixing together at least one organic polyamine with urea and with at least one secondary amine,
 b) reacting the mixture obtained from a) in at least one following residence reactor or two or more residence reactors,
 c) removing a resultant ammonia at the same time as the reaction course in stage b) or subsequently,
 d) removing an excess secondary amine, and other by-components which boil at temperatures lower than said polyureas, from the discharge from b),
 f) in a continuous dissociation apparatus, dissociating said polyureas into a corresponding isocyanate and secondary amine, to give at least one isocyanate-containing stream and at least one secondary amine-containing stream, g) purifying the isocyanate-containing stream obtained from the dissociation f) by
   g1) removing solvent, if solvent was used beforehand,
   g2a) in the case of distillable isocyanates, subjecting them to distillative purification, or
   g2b) in the case of undistillable isocyanates, subjecting them to optional purification by nondistillative means,
and
i) purifying the secondary amine-containing stream obtained from the dissociation f) and optionally recycling it.

2. The process according to claim 1, wherein the polyamine is a diamine.

3. The process according to claim 1, wherein the polyamine is at least one polyamine selected from the group consisting of butane-1,4-diamine, pentane-1,5-diamine, 2-ethylbutane-1,4-diamine, octane-1,8-diamine, decane-1,10-diamine, dodecane-1,12-diamine, cyclohexane-1,4-diamine, 2-methyl-, 4-methylcyclohexane-1,3-diamine, 1,3- and 1,4-diaminomethylcyclohexane, 4,4'- or 2,4'-di(isocyanatocyclohexyl)methane, hexane-1,6-diamine and 3-aminomethyl-3,5,5-trimethylcyclohexylamine.

4. The process according to claim 1, wherein the polyamine is at least one polyamine selected from the group consisting of 2,4- and 2,6-tolylenediamine, 4,4'-, 2,4'- and 2,2'-diaminodiphenylmethane and the isomer mixtures thereof, and also polyamine mixtures of the diphenylmethane series which are obtainable by polycondensation of formaldehyde with aniline.

5. The process according to any claim 1, wherein the secondary amine is of the formula $HNR^1R^2$ in which $R^1$ and $R^2$ independently of one another may denote alkyl having 1 to 20 carbon atoms, cycloalkyl having 3 to 12 carbon atoms, aryl having 6 to 14 carbon atoms, or an aralkyl radical which has 6 to 14 carbon atoms in the aryl and 1 to 6 carbon atoms in the alkyl radical, or the radicals $R^1$ and $R^2$ together may form a ring which including the nitrogen atom is five- to twelve-membered, it being possible for the radicals additionally to have ether groups.

6. The process according to claim 1, wherein the secondary amine is at least one secondary amine selected from the group consisting of dimethylamine, diethylamine, di-n-propylamine, diisopropylamine, di-n-butylamine, dihexylamine, dioctylamine, ethylmethylamine, isopropylmethylamine, n-butylmethylamine, tert-butylmethylamine, isopropylethylamine, n-butylethylamine, tert-butylethylamine, morpholine, piperidine and pyrrolidine.

7. The process according to claim 1, wherein steps a) and b) are carried out in a common apparatus.

8. The process according to claim 1, wherein polyamine, urea, and secondary amine are mixed and reacted at a molar ratio of from 1:2 to 20:5 to 40, at temperatures of 50-300° C. under a pressure of 0.1 to 30 bar.

9. The process according to claim 1, wherein step f) is carried out in the presence of an organic or inorganic Brønsted acid.

10. The process according to claim 1, wherein step f) is carried out in the presence of at least one solvent selected from the group consisting of hexane, benzene, nitrobenzene, anisole, chlorobenzene, chlorotoluene, o-dichlorobenzene, trichlorobenzene, diethyl isophthalate (DEIP), tetrahydrofuran (THF), dimethylformamide (DMF), xylene, chloronaphthalene, decahydronaphthalene and toluene.

11. The process according to claim 1, wherein the secondary amine in step i) is liberated by means of a base.

12. The process according to claim 11, wherein ammonia liberated in step c) is used at least partly as base in step i).

13. The process according to claim 1, wherein the secondary amine is liberated in step i) by a thermal separation from the salt formed with the acid.

14. The process according to claim 1, wherein the dissociation in step f) is carried out in the presence of at least one gaseous acid in a mixing pump or in a nozzle mixing device.

15. The process according to claim 1, wherein said at least one organic polyamine and said urea are mixed in the presence of at least one catalyst.

16. The process according to claim 1, wherein said at least one organic polyamine and said urea are mixed in the absence of a catalyst.

* * * * *